United States Patent
Merget et al.

(10) Patent No.: US 8,907,028 B2
(45) Date of Patent: Dec. 9, 2014

(54) AQUEOUS MIXTURES COMPRISING AMINOALKYL-CONTAINING POLYORGANOSILOXANES AND SILICONE RESINS

(75) Inventors: Markus Merget, Mehring (DE);
Richard Becker, Burghausen (DE);
Franz Wimmer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/821,333

(22) PCT Filed: Sep. 12, 2011

(86) PCT No.: PCT/EP2011/065769
§ 371 (c)(1),
(2), (4) Date: Mar. 7, 2013

(87) PCT Pub. No.: WO2012/038293
PCT Pub. Date: Mar. 29, 2012

(65) Prior Publication Data
US 2013/0177517 A1     Jul. 11, 2013

(30) Foreign Application Priority Data
Sep. 20, 2010   (EP) .................................. 10177523

(51) Int. Cl.
| | | |
|---|---|---|
| C08F 283/12 | (2006.01) |
| A61K 8/06 | (2006.01) |
| C08L 83/08 | (2006.01) |
| A61K 8/898 | (2006.01) |
| C09D 183/08 | (2006.01) |
| D06M 15/643 | (2006.01) |
| A61Q 5/12 | (2006.01) |
| C08L 83/04 | (2006.01) |
| C08G 77/04 | (2006.01) |
| C08G 77/26 | (2006.01) |

(52) U.S. Cl.
CPC ................. *A61K 8/062* (2013.01); *C08L 83/08* (2013.01); *A61K 8/898* (2013.01); *C09D 183/08* (2013.01); *D06M 15/6436* (2013.01); *A61Q 5/12* (2013.01); *C08L 83/04* (2013.01); *C08G 77/04* (2013.01); *C08G 77/26* (2013.01)
USPC ........................................................ 525/477

(58) Field of Classification Search
None
See application file for complete search history.

(56) References Cited

U.S. PATENT DOCUMENTS

| | | | |
|---|---|---|---|
| 6,326,061 B1 * | 12/2001 | Lautenschlager et al. ..... 427/394 |
| 2006/0041026 A1 | 2/2006 | Mahr et al. |
| 2007/0128962 A1 | 6/2007 | Serobian |
| 2011/0015332 A1 | 1/2011 | Martin et al. |

FOREIGN PATENT DOCUMENTS

| | | |
|---|---|---|
| CN | 101506274 A | 8/2009 |
| DE | 10 2006 032 456 A1 | 2/2007 |
| WO | 2006/097207 A1 | 9/2006 |
| WO | 2006/097227 A2 | 9/2006 |
| WO | 2006/097227 A3 | 9/2006 |

* cited by examiner

*Primary Examiner* — Ernest V Arnold
*Assistant Examiner* — Kauser M Akhoon
(74) *Attorney, Agent, or Firm* — Brooks Kushman P.C.

(57) ABSTRACT

Aqueous emulsions of organopolysiloxanes functionalized with a limited amount of aminoalkyl-functional end groups and silicone resins are storage stable, yet capable of adequate crosslinking upon application to substances to be hydrophobicized.

13 Claims, No Drawings

AQUEOUS MIXTURES COMPRISING AMINOALKYL-CONTAINING POLYORGANOSILOXANES AND SILICONE RESINS

CROSS-REFERENCE TO RELATED APPLICATIONS

This application is the U.S. national phase of PCT Appln. No. PCT/EP2011/065769 filed Sep. 12, 2011 which claims priority to European application 10177523.7 filed Sep. 20, 2010, the disclosures of which are incorporated in their entirety by reference herein.

BACKGROUND OF THE INVENTION

1. Field of the Invention

The invention relates to water-containing mixtures comprising aminoalkyl-containing polyorganosiloxanes, silicone resins, protonating agents and water, and also to a process for the preparation thereof.

2. Description of the Related Art

Aqueous compositions comprising amino-functional organopolysiloxanes are known. Such compositions are used for example for hydrophobicizing treatment of natural and/or synthetic textile fibres, for hydrophobicizing treatment of building products, as a constituent of care agents and as a constituent of cosmetic preparations.

Patents cited hereinbelow all have in common that they concern aqueous mixtures of MQ resins and silicone oils. WO2006097207 and WO2006097227 describe aqueous emulsions consisting of polydimethylsiloxanes and silicone resins for treatment of fibres and for reducing wrinkling. US2007128962 utilizes an aqueous mixture of polydimethylsiloxane, MQ resin and a volatile silicone solvent for imparting resistance to stain absorption.

US 20060041026 and DE102006032456 describe the treatment of textile fibres with oil-in-water emulsions of aminoalkyl-containing polydimethylsiloxanes of low emulsifier content. However, these mixtures have the disadvantage that the excessively low proportion of reactive end groups leads to poor crosslinking.

SUMMARY OF THE INVENTION

The present invention provides water-containing mixtures (M) comprising 1) 100 parts by weight of one or more liquid aminoalkyl-containing polyorganosiloxanes (P) comprising at least 80 mol % of units selected from units of the general formulae Ia, Ib, II and III $$R^1_2SiO_{(4-a-b)/2} \quad (Ia),$$

$$R^3_3SiO_{(1/2)} \quad (II),$$

where
a has the value 0 or 1,
b has the value 1 or 2,
a+b has a value of 2,
$R^1$ represents monovalent hydrocarbyl radicals having 1-40 carbon atoms and optionally substituted with halogens, $R^2$ represents either
a) aminoalkyl radicals of the general formula IV $$-R^5-NR^6R^7 \quad (IV)$$

where
$R^5$ represents divalent hydrocarbyl radicals having 1-40 carbon atoms,
$R^6$ represents monovalent hydrocarbyl radicals having 1-40 carbon atoms, H, hydroxymethyl or alkanoyl radicals, and
$R^7$ represents a radical of the general formula V $$-(R^8-NR^6)_xR^6 \quad (V)$$

where
x has the value 0 or an integer value from 1 to 40, and
$R^8$ represents a divalent radical of the general formula VI $$-(CR^9_2-)_y \quad (VI)$$

where
y has an integer value from 1 to 6, and
$R^9$ represents H or hydrocarbyl radicals having 1-40 carbon atoms, or
b) in the general formula IV $R^6$ and $R^7$ combine with the nitrogen atom to form a cyclic organic radical having 3 to 8 —CH$_2$— units, although nonadjacent —CH$_2$— units may be replaced by units selected from —C(=O)—, —NH—, —O— and —S—,
$R^3$ represents hydrocarbyl radicals having 1-40 carbon atoms and optionally substituted with halogens,
$R^4$ represents —OR or —OH radicals, and
wherein, in the polyorganosiloxanes (P), the average ratio of the sum of units of the general formulae Ia and Ib to the sum of units of the general formulae II and III is in the range from 0.5 to 500, the average ratio of units II to III being in the range from 1.86 to 100, and the polyorganosiloxanes (P) have an average amine number of at least 0.01 mequiv/g, 2) at least 1 part by weight of one or more silicone resins (S) which each comprise at least 80 mol % of units selected from units of the general formulae VII, VIII, IX and X $$R^{10}_3SiO_{1/2} \quad (VII),$$

$$R^{10}_2SiO_{2/2} \quad (VIII),$$

$$R^{10}SiO_{3/2} \quad (IX),$$

$$SiO_{4/2} \quad (X),$$

where
$R^{10}$ represents hydrocarbyl radicals having 1-40 carbon atoms and optionally substituted with halogens, or H, —OR or —OH radicals,
at least 20 mol % of the units are selected from units of the general formulae IX and X
and at most 10% by weight of the $R^{10}$ radicals are —OR and —OH radicals, 3) protonating agent,
4) at least 10 parts by weight of water, and
5) at most 5 parts by weight of emulsifier.

DETAILED DESCRIPTION OF THE PREFERRED EMBODIMENTS

Using aminoalkyl-containing polyorganosiloxanes (P) having a certain ratio between nonreactive end groups of the general formula II and reactive end groups of the general formula III ensures that these water-containing mixtures (M) are storable for at least 3 months, yet still have a sufficient number of reactive end groups to provide adequate crosslinking to form an elastic film. These elastic films have a strong hydrophobicizing effect on surfaces.

The water-containing mixtures (M) are preferably oil-in-water emulsions.

The monovalent hydrocarbyl radicals R, $R^1$, $R^3$, $R^6$, $R^9$ and $R^{10}$ may be halogen substituted, linear, cyclic, branched, aromatic, saturated or unsaturated. Preferably, the monovalent hydrocarbyl radicals R, $R^1$, $R^3$, $R^6$, $R^9$ and $R^{10}$ each have 1 to 6 carbon atoms, and particular preference is given to alkyl radicals and phenyl radicals. Preferred halogen substituents are fluorine and chlorine. Particularly preferred monovalent hydrocarbyl radicals R, $R^1$, $R^3$, $R^6$, $R^9$ and $R^{10}$ are methyl, ethyl, and phenyl.

The divalent hydrocarbyl radicals $R^5$ may be halogen substituted, linear, cyclic, branched, aromatic, saturated or unsaturated. Preferably, the $R^5$ radicals have 1 to 10 carbon atoms, and particular preference is given to alkylene radicals having 1 to 6 carbon atoms, in particular propylene. Preferred halogen substituents are fluorine and chlorine.

Preferred $R^6$ radicals are alkyl and alkanoyl radicals. Preferred halogen substituents are fluorine and chlorine. Preferred alkanoyl radicals are $—C(=O)R^{11}$, where $R^{11}$ has the meanings and preferred meanings of $R^1$. Particularly preferred substituents $R^6$ are methyl, ethyl, cyclohexyl, acetyl and H. It is particularly preferable for the $R^6$ and $R^7$ radicals to be hydrogen.

Preferred cyclic organic radicals formed from $R^6$ and $R^7$ in the general formula IV together with the attached nitrogen atom are five and six membered rings, in particular the residues of pyrrolidine, pyrrolidin-2-one, pyrrolidine-2,4-dione, pyrrolidin-3-one, pyrazol-3-one, oxazolidine, oxazolidin-2-one, thiazolidine, thiazolidin-2-one, piperidine, piperazine, piperazine-2,5-dione and morpholine.

Particularly preferred $R^2$ radicals are $—CH_2NR^6R^7$, $—(CH_2)_3NR^6R^7$ and $—(CH_2)_3N(R^6)(CH_2)_2N(R^6)_2$. Examples of particularly preferred $R^2$ radicals are aminoethylaminopropyl and cyclohexylaminopropyl.

Preference is also given to mixtures (M) wherein at least 1 mol %, more preferably at least 5 mol %, and most preferably at least 20 mol % and at most 90 mol %, more preferably at most 70 mol % and most preferably at most 60 mol % of the $R^6$ and $R^7$ radicals are acetyl radicals and the remaining $R^6$ and $R^7$ radicals are hydrogen.

Preferably, b is 1. Preferably, a+b has an average value from 1.9 to 2.2.

Preferably, x is 0 or a value from 1 to 18, more preferably 1 to 6.

Preferably, y is 1, 2 or 3.

Preferably, the polyorganosiloxanes (P) comprise at least 3 and more preferably least 10 units of the general formula I.

Preferably, the liquid aminoalkyl-containing polyorganosiloxanes (P) comprise at least 95 mol %, more preferably at least 98 mol % and most preferably at least 99.5 mol % of units selected from units of the general formulae I, II and III.

Further units of the polyorganosiloxanes (P) can be selected for example from units selected from units of the general formulae IX and X.

The ratio of a to b is chosen such that the polyorganosiloxanes (P) preferably have an amine number of at least 0.1, in particular at least 0.3 mequiv/g of polyorganosiloxane (P). The amine number of the polyorganosiloxanes (P) is preferably at most 7, more preferably at most 4.0 and in particular at most 3.0 mequiv/g of polyorganosiloxane (P).

The amine number designates the number of ml of 1N HCl which are required for neutralizing 1 g of polyorganosiloxane (P).

The viscosity of the polyorganosiloxanes (P) is preferably at least 1 and more preferably at least 10 mPa·s and preferably at most 100,000 and particularly at most 10,000 mPa·s at 25° C.

The ratio of the units of the general formulae I to the sum total of II and III is preferably at least 10, more preferably at least 50 and preferably at most 250, more preferably at most 150.

The ratio of units II to III is preferably at least 1.9 and more preferably at least 2.0 and preferably at most 70 and more preferably at most 50.

The polyorganosiloxanes (P) are obtainable via known chemical processes such as, for example, hydrolysis or equilibration.

The mixtures (M) preferably comprise at least 5 and more preferably at least 10 parts by weight and preferably at most 100, more preferably at most 50 and most preferably at most 30 parts by weight of silicone resins (S).

The silicone resins (S) preferably comprise preferably at least 95 mol % and more preferably at least 98 mol % of units of the general formulae VII to X.

The silicone resins (S) are preferably MQ silicone resins (MQ) comprising at least 80 mol % of units, preferably at least 95 mol % and more preferably at least 97 mol % of units of the general formulae VII and X. The average ratio of units of the general formulae VII to X is preferably at least 0.25, more preferably at least 0.5 and preferably 4, more preferably at most 1.5.

The silicone resins (S) are also preferably DT silicone resins (DT) comprising at least 80 mol % of units, preferably at least 95 mol % and most preferably at least 97 mol % of units of the general formulae VIII and IX. The average ratio of units of the general formulae VIII to IX is preferably at least 0.01, more preferably at least 0.02 and preferably at most 3.5, more preferably at most 0.5.

Preferably, at most 8% by weight of the $R^{10}$ radicals are selected from —OR and OH.

The average molecular weight Mn of the silicone resins (S) is preferably at least 200 g/mol and more preferably at least 1000 g/mol and preferably at most 100,000 g/mol and more preferably at most 20,000 g/mol.

The water-containing mixtures (M) utilize minimal amounts of emulsifiers and preferably no emulsifiers. This provides a distinctly improved hydrophobic effect. The impregnation achieved therewith is at least as good as that hitherto only achievable with solvent-containing formulations.

The mixtures (M) are homogeneous, stable and dilution stable without further addition of other stabilizing ingredients, such as emulsifiers or silicone-polyether copolymer emulsifiers. Their emulsifier content is preferably at most 3 parts by weight, more preferably at most 1 part by weight and most preferably at most 0.1 part by weight.

Examples of emulsifiers are sorbitan esters of fatty acids having 10 to 22 carbon atoms; polyoxyethylene sorbitan esters of fatty acids having 10 to 22 carbon atoms and an ethylene oxide content of up to 35 percent; polyoxyethylene sorbitan esters of fatty acids having 10 to 22 carbon atoms; polyoxyethylene derivatives of phenols having 6 to 20 carbon atoms on the aromatic and an ethylene oxide content of up to 95 percent; fatty amino- and amidobetaines having 10 to 22 carbon atoms; polyoxyethylene condensates of fatty acids or fatty alcohols having 8 to 22 carbon atoms with an ethylene oxide content of up to 95 percent; fatty amine oxides having 10 to 22 carbon atoms; fatty imidazolines having 6 to 20 carbon atoms; fatty amidosulfobetaines having 10 to 22 carbon atoms; quarternary emulsifiers, such as fatty ammonium compounds having 10 to 22 carbon atoms; fatty morpholine oxides having 10 to 22 carbon atoms; alkali metal salts of carboxylated, ethoxylated alcohols having 10 to 22 carbon atoms and up to 95 percent of ethylene oxide; ethylene oxide condensates of fatty acid monoesters of glycerol having 10 to 22 carbon atoms and up to 95 percent of ethylene oxide; mono- and diethanolamides of fatty acids having 10 to 22 carbon atoms; phosphate esters.

It is well known in the area of emulsifiers, the counter ions in the case of cationic emulsifiers is a halide, sulfate or methylsulfate. Chlorides are the most industrially available compounds.

The abovementioned fatty structures are usually the lipophilic half of the emulsifiers. A customary fatty group is an alkyl group of natural or synthetic origin. Known unsaturated groups are the oleyl, linoleyl, decenyl, hexadecenyl and dodecenyl radicals. Alkyl groups may be cyclic, linear or branched. Other possible emulsifiers are sorbitol monolaurate/ethylene oxide condensates; sorbitol monomyristate/ethylene oxide condensates; sorbitol monostearate/ethylene oxide condensates; dodecylphenol/ethylene oxide condensates; myristylphenol/ethylene oxide condensates; octylphenyl/ethylene oxide condensates; stearylphenol ethylene oxide condensates; lauryl alcohol/ethylene oxide condensates; stearyl alcohol/ethylene oxide condensates; decylaminobetaine; cocoamidosulfobetaine; olylamidobetaine; cocoimidazoline; cocosulfoimidazoline; cetylimidazoline; 1-hydroxyethyl-2-heptadecenylimidazoline; n-cocomorpholine oxide; decyldimethylamine oxide; cocoamidodimethylamine oxide; sorbitan tristearate having condensed ethylene oxide groups; sorbitan trioleate having condensed ethylene oxide groups; trimethyldodecylammonium chloride; trimethylstearylammonium methosulfate.

The protonating agent is preferably a monoprotic or multiprotic, water-soluble or water-insoluble, organic or inorganic acid. Particular preference is given to formic acid, acetic acid, sulphuric acid, phosphoric acid, hydrochloric acid, citric acid or mixtures thereof. Protonating agents are preferably added in amounts of at least 0.05 and more preferably at least 0.2, and preferably at most 2 and more preferably at most 1.5 mol of proton per mole of basic nitrogen atom in the $R^2$ radicals.

The pH value is adjusted by the protonating agent preferably to at least 2.0, more preferably to at least 2.8 and most preferably at least 3.5 and preferably at most 8, more preferably at most 7.2 and most preferably at most 6.5.

The water is preferably completely ion-free or salt-containing water, more preferably completely ion-free water.

In addition to the combination of polyorganosiloxane (P) and room temperature solid organopolysiloxanes, the mixtures (M) may additionally comprise further silicones, for example liquid silicones, silicone waxes, cyclic silicones or solid silicones. When further silicones are used, then they are preferably used in amounts of at least 10.0 and at most 90.0 parts by weight, more preferably at most 60.0 parts by weight, all based on 100 parts by weight of polyorganosiloxane (P).

Preferably, the mixtures (M) include auxiliaries (H) selected from mono- or polyalcohols and ethers thereof which have a boiling point or boiling range of at most 260° C. at 0.10 MPa.

Examples of monoalcohols are ethanol, n-propanol, isopropanol and butanol. Examples of polyalcohols are ethylene glycol and propylene glycol. Examples of polyalcohol ethers are ethylene glycol monobutyl ether, ethylene glycol monoethyl ether and diethylene glycol monoethyl ether.

The mixtures (M) include preferably at least 0.1 and more preferably at least 10 parts by weight of auxiliaries (H) and preferably at most 100 and more preferably at most 60 parts by weight of auxiliaries.

The mixtures (M) may additionally include further substances, such as preservatives, scents, corrosion inhibitors, protective colloids (PC) and dyes.

Suitable protective colloids (PC) are polyvinyl alcohols; polyvinyl acetals; polyvinylpyrrolidones; polysaccharides in water-soluble form, such as starches (amylose and amylopectin), celluloses and the carboxymethyl, methyl, hydroxyethyl and hydroxypropyl derivatives thereof, dextrins and cyclodextrins; proteins, such as casein or caseinate, soybean protein, gelatin; ligninsulfonates; synthetic polymers, such as poly(meth)acrylic acid, copolymers of (meth)acrylates with carboxy-functional comonomer units, poly(meth)acrylamide, polyvinylsulfonic acids and the water-soluble copolymers thereof; melamine formaldehyde sulfonates, naphthalene formaldehyde sulfonates, styrene-maleic acid and vinyl ether-maleic acid copolymers; cationic polymers, such as poly-DADMAC.

Partly hydrolyzed or completely hydrolyzed polyvinyl alcohols having a degree of hydrolysis of from 80 to 100 mol %, in particular partly hydrolyzed polyvinyl alcohols having a degree of hydrolysis of from 80 to 95 mol % are preferred. Examples of these are partly hydrolyzed copolymers of vinyl acetate with hydrophobic comonomers, such as isopropenyl acetate, vinyl pivalate, vinyl ethylhexanoate, vinyl esters of saturated alpha-branched monocarboxylic acids having 5 or 9 to 11 C atoms, dialkyl maleates and dialkyl fumarates, such as diisopropyl maleate and diisopropyl fumarate, vinyl chloride, vinyl alkyl ethers, such as vinyl butyl ether, olefins, such as ethene and decene. Examples of such vinyl esters are those which are offered as vinyl versatate under the designations VeoVa®5, VeoVa®9, VeoVa®10 and VeoVa$^{11}$. The proportion of the hydrophobic units is preferably from 0.1 to 10% by weight, based on the total weight of the partly hydrolyzed polyvinyl alcohol. It is also possible to use mixtures of said polyvinyl alcohols.

Further polyvinyl alcohols which are most preferred are partly hydrolyzed, hydrophobized polyvinyl acetates which are obtained by polymer-analogous reaction, for example acetalation of the vinyl alcohol units with $C_1$- to $C_4$-aldehydes, such as butyraldehyde. The proportion of the hydrophobic units is preferably from 0.1 to 10% by weight, based on the total weight of the partly hydrolyzed polyvinyl acetate. The degree of hydrolysis is from 80 to 95 mol %, preferably from 85 to 94 mol %. Said protective colloids (PC) are obtainable by means of processes known to the person skilled in the art.

The mixtures (M) preferably include at most 50 parts by weight and more preferably at most 30 parts by weight and preferably at least 0.1 part by weight of such protective colloids (PC).

Examples of preservatives are alcohols, formaldehyde, parabens, benzyl alcohol, propionic acid and salts thereof and also isothiazolinones.

The mixtures (M) may further include yet other additives, such as non-silicon-containing oils and waxes. Examples thereof are rapeseed oil, olive oil, mineral oil, paraffin oil or non-silicon-containing waxes, for example carnauba wax and candelilla wax or montan acid and montan ester waxes, incipiently oxidized synthetic paraffins, polyethylene waxes, polyvinyl ether waxes and metal-soap-containing waxes, of which carnauba waxes, paraffin wax and polyethylene waxes are preferred and paraffin waxes are particularly preferred. The mixtures (M) preferably include at most 30.0 parts by weight and more preferably at most 10 parts by weight and preferably at least 0.1 part by weight of such additives.

The mixtures (M) are obtainable by mixing polyorganosiloxane (P), silicone resins (S), protonating agent, water and optoionally auxiliaries (H), protective colloids (PC), further substances and additives in any desired order.

The mixing is preferably performed at a temperature of at least 10° C. and more preferably at least 15° C. and preferably at most 80° C. and more preferably at most 40° C., and at a pressure of preferably 900 to 1100 hPa. However, the mixing can also be carried out at higher or lower pressures.

The mixtures (M) are preferably prepared by diluting mixtures (M1), comprising polyorganosiloxane (P) and silicone resins (S) and optionally auxiliaries (H), protective colloids (PC) and also at most 5 parts by weight of water, with water. The mixtures (M1) already have a favourable ratio between reactive and nonreactive end groups and are storable for at least 3 months in the absence of atmospheric humidity. The fact that these mixtures (M1) are storable appreciably simplifies the logistics involved in the synthesis of the mixtures (M). There is thus no need for immediate conversion of the water-free mixtures (M1) into mixtures (M).

The mixtures (M) are dilutable with water in any proportion. The mixtures (M) may preferably include water in amounts of at least 10.0 parts by weight, more preferably at least 100.0 parts by weight and preferably at most 5000 parts by weight and most preferably at most 1000 parts by weight.

Irrespective of their water content, the mixtures (M) are clear or slightly opaque liquids preferably having a viscosity at 25° C. of at least 5 and more preferably at least 10 $mm^2/s$ and preferably at most 10,000, more preferably at most 1000 and most preferably at most 500 $mm^2/s$.

The mixtures (M) are useful as hydrophobicizers for surfaces, preferably hard and soft porous surfaces such as, for example, wood, textiles, leather, hair, skin and stone. The impregnation of textiles which is achieved with the mixtures (M) is durable to laundering in that it will withstand many wash cycles.

All the above symbols in the above formulae each have their meanings independently of each other. The silicon atom is tetravalent in all the formulae.

In the examples which follow, unless otherwise stated, all quantitative and percentage recitations are by weight, all pressures are equal to 0.10 MPa (absolute) and all temperatures are equal to 20° C.

The water used in the examples is characterized as follows: The water is completely ion-free or salt-containing water, preferably completely ion-free water.

EXAMPLES

1. Preparation of a Stable Oil Mixture 13.2 g of MQ silicone resin ($\{[Me_3SiO_{1/2}]_{0.373}[SiO_2]_{0.627}\}_{40}$, Mn=2700 g/mol, resin contains 0.2% OH and 3.1% OEt [corresponds to $R^{10}$]) are dissolved in 10.5 g of ethylene glycol monohexyl ether (obtainable from Sigma-Aldrich Chemie GmbH) by stirring and subsequently admixed with 76.3 g of amine oil (viscosity about 1000 $mm^2/s$ at 25° C. [corresponds to Ia+Ib+II+III=230], functional radicals —$(CH_2)_3NH(CH_2)NH_2$ [corresponds to $R^2$], amine number of 0.6 mmol/g, 90 mol % $SiMe_3$ end groups, 10 mol % $SiMe_2OH$ end groups [corresponds to II/III=9,0]) at 25° C. to obtain a clear, colourless solution having a viscosity of about 3000 mPa·s. This mixture is stable for a period of 3 months.

2. Preparation of a Stable Oil Mixture 13.2 g of MQ silicone resin ($\{[Me_3SiO_{1/2}]_{0.373}[SiO_2]_{0.627}\}_{40}$, Mn=2700 g/mol, resin contains 0.2% OH and 3.1% OEt [corresponds to $R^{10}$]) are dissolved in 10.5 g of ethylene glycol monohexyl ether (obtainable from Sigma-Aldrich Chemie GmbH) by stirring and subsequently admixed with 76.3 g of amine oil (viscosity about 500 $mm^2/s$ at 25° C. [corresponds to Ia+Ib+II+III=170], functional radicals —$(CH_2)_3NH(CH_2)NH_2$ [corresponds to $R^2$], amine number of 0.6 mmol/g, 68 mol % $SiMe_3$ end groups, 25 mol % $SiMe_2OH$ end groups, 7 mol % $SiMe_2OMe$ end groups [corresponds to II/III=2,1]) at 25° C. to obtain a clear, colourless solution having a viscosity of about 3000 mPa·s. This mixture is stable for a period of 3 months.

3. Preparation of a Stable Oil Mixture 13.2 g of MQ silicone resin ($\{[Me_3SiO_{1/2}]_{0.373}[SiO_2]_{0.627}\}_{40}$, Mn=2700 g/mol, resin contains 0.2% OH and 3.1% OEt [corresponds to $R^{10}$]) are dissolved in 10.5 g of ethylene glycol monohexyl ether (obtainable from Sigma-Aldrich Chemie GmbH) by stirring and subsequently admixed with 76.3 g of amine oil (viscosity about 950 $mm^2/s$ at 25° C. [corresponds to Ia+Ib+II+III=220], functional radicals —$(CH_2)_3NH(CH_2)NH_2$ [corresponds to $R^2$], amine number of 0.6 mmol/g, 92 mol % $SiMe_3$ end groups, 7 mol % $SiMe_2OH$ end groups, 1 mol % $SiMe_2OMe$ end groups [corresponds to II/III=11,5]) at 25° C. to obtain a clear, colourless solution having a viscosity of about 3000 mPa·s. This mixture is stable for a period of 3 months.

4. Preparation of a Stable Oil Mixture 13.2 g of MQ silicone resin ($\{[Me_3SiO_{1/2}]_{0.373}[SiO_2]_{0.627}\}_{40}$, Mn=2700 g/mol, resin contains 0.2% OH and 3.1% OEt [corresponds to $R^{10}$]) are dissolved in 10.5 g of ethylene glycol monohexyl ether (obtainable from Sigma-Aldrich Chemie GmbH) by stirring and subsequently admixed with 76.3 g of amine oil (viscosity about 2500 $mm^2/s$ at 25° C. [corresponds to Ia+Ib+II+III=315], functional radicals —$(CH_2)_3NH(CH_2)NH_2$ [corresponds to $R^2$], amine number of 0.8 mmol/g, 72 mol % $SiMe_3$ end groups, 26 mol % $SiMe_2OH$ end groups, 2 mol % $SiMe_2OMe$ end groups [corresponds to II/III=2,6]) at 25° C. to obtain a clear, colourless solution having a viscosity of about 3000 mPa·s. This mixture is stable for a period of 3 months.

5. Preparation of a Stable Oil Mixture 3.5 g of MQ silicone resin ($\{[Me_3SiO_{1/2}]_{0.373}[SiO_2]_{0.627}\}_{40}$, Mn=2700 g/mol, resin contains 0.2% OH and 3.1% OEt [corresponds to $R^{10}$]) are mixed for 30 minutes with 20.2 g of amine oil (viscosity about 225 $mm^2/s$ at 25° C. [corresponds to Ia+Ib+II+III=105], functional radicals —$(CH_2)_3NH(CH_2)NH_2$ [corresponds to $R^2$], amine number of 2.6 mmol/g, 94 mol % $SiMe_3$ end groups, 5 mol % $SiMe_2OH$ end groups, 1 mol % $SiMe_2OMe$ end groups [corresponds to II/III=15,7]).

6. Preparation of a Stable Oil Mixture 5.9 g of DT silicone resin solution ($\{[Me_2SiO]_{0.03}[MeSiO_{3/2}]_{0.97}\}_{33}$, Mn=2300 g/mol, resin contains 0.4% OH and 4.4% OEt [corresponds to $R^{10}$], 25% in Shellsol T) are disolved in 3.6 g ethylene glycol monohexyl ether (obtainable from Sigma-Aldrich Chemie GmbH) by stirring and subsequently admixed with 14.2 g of amine oil (viscosity about 1000 mm²/s at 25° C. [corresponds to Ia+Ib+II+III=230], functional radicals —(CH₂)₃NH(CH₂)NH₂ [corresponds to R²], amine number of 0.6 mmol/g, 90 mol % SiMe₃ end groups, 10 mol % SiMe₂OH end groups [corresponds to II/III=9,0]) at 25° C. to obtain a clear, colourless solution having a viscosity of about 3000 mPa·s. This mixture is stable for a period of 3 months.

7. Preparation of an Unstable Oil Mixture 13.2 g of MQ silicone resin ({[Me₃SiO_{1/2}]_{0.373} [SiO₂]_{0.627}}₄₀, Mn=2700 g/mol, resin contains 0.2% OH and 3.1% OEt [corresponds to R¹⁰]) are dissolved in 10.5 g of ethylene glycol monohexyl ether (obtainable from Sigma-Aldrich Chemie GmbH) by stirring and subsequently admixed with 76.3 g of amine oil (viscosity about 2800 mm²/s at 25° C. [corresponds to Ia+Ib+II+III=325], functional radicals —(CH₂)₃NH(CH₂)NH₂ [corresponds to R²], amine number of 0.6 mmol/g, 47 mol % SiMe₃ end groups, 45 mol % SiMe₂OH end groups, 8 mol % SiMe₂OMe end groups [corresponds to II/III=0.9]) at 25° C. to obtain a clear, colourless solution having a viscosity of about 3000 mPa·s. This mixture has formed a gel after 3 d, the preparation of an emulsion is only possible within these three days.

8. Preparation of an Unstable Oil Mixture 13.2 g of MQ silicone resin ({[Me₃SiO_{1/2}]_{0.373} [SiO₂]_{0.627}}₄₀, Mn=2700 g/mol, resin contains 0.2% OH and 3.1% OEt [corresponds to R¹⁰]) are dissolved in 10.5 g of ethylene glycol monohexyl ether (obtainable from Sigma-Aldrich Chemie GmbH) by stirring and subsequently admixed with 76.3 g of amine oil (viscosity about 2900 mm²/s at 25° C. [corresponds to Ia+Ib+II+III=331], functional radicals —(CH₂)₃NH(CH₂)NH₂ [corresponds to R²], amine number of 0.4 mmol/g, 47 mol % SiMe₃ end groups, 47 mol % SiMe₂OH end groups, 6 mol % SiMe₂OMe end groups [corresponds to II/III=0.9]) at 25° C. to obtain a clear, colourless solution having a viscosity of about 3000 mPa·s. This mixture has formed a gel after 3 d, the preparation of an emulsion is only possible within these three days.

Preparation of Emulsions

General prescription for the emulsification of the oil mixtures 1 to 6:

8.0 g of demineralized water, 12.0 g of diethylene glycol monobutyl ether (obtainable from Sigma-Aldrich Chemie GmbH), 1.5 g of diethylene glycol monohexyl ether (obtainable from Sigma-Aldrich Chemie GmbH) and acetic acid 100% (equimolar to the amine groups of the aminoalkyl-containing polyorganosiloxanes, obtainable from VWR International) are initially charged and mixed at room temperature, then 39.0 g of the above-described oil mixture are added at room temperature and subsequently a further 46.5 g of demineralized water are added with stirring to obtain an almost clear, colourless emulsion. Oil mixtures 5 and 6 were emulsified immediately after their preparation.

General prescription for the emulsification of the oil mixtures 1 and 2 in presence of polyvinyl alcohol:

17 g polyvinyl alcohol "Celvol 523" (obtainable from Sekisui Specialty Chemicals America), 10% in water, 23 g polyvinyl alcohol M05/140 M, 20% in water (obtainable from Wacker Chemie AG) and 4.0 g diethylenglykol monohexylether (obtainable from Sigma-Aldrich Chemie GmbH) are initially charged and mixed at room temperature, then 39.0 g of the above-described oil mixture are added at room temperature and subsequently 29.0 g of demineralized water are added with stirring to obtain an opaque, colourless emulsion.

Storage Tests of Emulsions at 50° C.

The emulsions are stored in closed vessels at 50° C. for 3 months. The samples are visually assessed daily for homogeneity. The breaking of the emulsions takes place in various phases:

phase 1: emulsion becomes cloudy, but can be turned clear again by shaking
phase 2: emulsion becomes cloudy, can no longer be returned to clear by shaking
phase 3: emulsion exhibits gel-type constituents

| Sample | Phase 1 start | Phase 2 start | Phase 3 start |
|---|---|---|---|
| Emulsion from oil mixture 1 | — | — | — |
| Emulsion from oil mixture 2 | 21 d | — | — |
| Emulsion from oil mixture 3 | — | — | — |
| Emulsion from oil mixture 4 | 24 d | — | — |
| Emulsion from oil mixture 5 | 42 d | — | — |
| Emulsion from oil mixture 6 | — | — | — |
| Emulsion from oil mixture 7* | 10 d | 21 d | 24 d |
| Emulsion from oil mixture 8* | 8 d | 16 d | 22 d |
| Emulsion from oil mixture 1 with polyvinyl alcohol | — | — | — |
| Emulsion from oil mixture 2 with polyvinyl alcohol | 42 d | — | — |

*not according to the invention
— had not occurred after 3 months

The invention claimed is:
1. Aqueous emulsions comprising:
1) 100 parts by weight of one or more liquid aminoalkyl-containing polyorganosiloxanes comprising at least 80 mol % of units of the formulae Ia, Ib II and III

$$R^1{}_2SiO_{(4-a-b)/2} \quad (Ia),$$

$$R^2{}_aR^2{}_bSiO_{(4-a-b)/2} \quad (Ib),$$

$$R^3{}_3SiO_{(1/2)} \quad (II), \text{ and}$$

$$R^3{}_2R^4SiO_{(1/2)} \quad (III),$$

where
a is 0 or 1,
b is 1 or 2,
a+b is 2,
R¹ are monovalent hydrocarbyl radicals having 1-40 carbon atoms optionally substituted with halogens,
R² are either
a) aminoalkyl radicals of the formula IV

$$—R^5—NR^6R^7 \quad (IV)$$

where
R⁵ are divalent hydrocarbyl radicals having 1-40 carbon atoms, $R^6$ are monovalent hydrocarbyl radicals having 1-40 carbon atoms, H, hydroxymethyl or alkanoyl radicals, and
$R^7$ are radicals of the general formula V $$-(R^8-NR^6)_xR^6 \qquad (V)$$

where
x is 0 or an integer from 1 to 40, and
$R^8$ are divalent radicals of the formula VI $$-(CR^9_2-)_y \qquad (VI)$$

where
y is from 1 to 6, and
$R^9$ are H or hydrocarbyl radicals having 1-40 carbon atoms, or
b) in the formula IV, $R^6$ and $R^7$ combine with the nitrogen atom to form a cyclic organic radical having 3 to 8 —$CH_2$— units, wherein nonadjacent —$CH_2$— units are optionally replaced by units selected from —C(=O)—, —NH—, —O— and —S—,
$R^3$ are hydrocarbyl radicals having 1-40 carbon atoms optionally substituted with halogens,
$R^4$ are —OR or —OH radicals, where R is a monovalent hydrocarbyl radical, and wherein, in the polyorganosiloxanes, the average ratio of the sum of units of the formulae Ia and Ib to the sum of units of the formulae II and III is in the range from 0.5 to 500, the average ratio of units II to III being in the range from 1.86 to 100, and the polyorganosiloxanes have an average amine number of at least 0.01 mequiv/g,
2) at least 1 part by weight of one or more silicone resins which each comprise at least 80 mol % of units of the formulae VII, VIII, IX and X $$R^{10}_3SiO_{1/2} \qquad (VII),$$

$$R^{10}_2SiO_{2/2} \qquad (VIII),$$

$$R^{10}SiO_{3/2} \qquad (IX), \text{ and}$$

$$SiO_{4/2} \qquad (X),$$

where
$R^{10}$ are hydrocarbyl radicals having 1-40 carbon atoms and optionally substituted with halogens, or H, —OR or —OH radicals,
at least 20 mol % of the units are selected from units of the formulae IX and X and at most 10% by weight of the $R^{10}$ radicals are —OR and —OH radicals, 3) protonating agent,
4) at least 10 parts by weight of water, and
5) at most 5 parts by weight of emulsifier,
the aqueous emulsions being storage stable for a period of at least three months at 50° C., wherein the monovalent hydrocarbyl radicals R, $R^1$, $R^3$, $R^6$, $R^9$ and $R^{10}$ are alkyl radicals having 1 to 6 carbon atoms or phenyl radicals.

2. The mixture of claim 1, wherein the silicone resins are MQ silicone resins comprising at least 80 mol % of units selected from units of the formulae VII and X and the average ratio of the units of the formulae VII to X is in the range from 0.25 to 4.

3. The mixture of claim 1, wherein the liquid aminoalkyl-containing polyorganosiloxanes comprise at least 95 mol % of units of the formulae Ia, Ib, II and III.

4. The mixture of claim , wherein the $R^2$ radicals are selected from the group consisting of —$CH_2NR^6R^7$, —$(CH_2)_3NR^6R^7$ and —$(CH_2)_3N(R^6)(CH_2)_2N(R^6)_2$.

5. The mixture of claim 4, wherein the radicals $R^6$ and $R^7$ are hydrogen radicals.

6. The mixture of claim 4, wherein 1 to 90 mol % of the $R^6$ and $R^7$ radicals are acetyl radicals and the remaining $R^6$ and $R^7$ radicals are hydrogen radicals.

7. The mixture of claim 1, wherein the viscosity of the polyorganosiloxanes is in the range from 10 mPa·s to 10,000 mPa·s at 25° C.

8. The mixture of claim 1, comprising 5 to 50 parts by weight of MQ silicone resins.

9. The mixture of claim 1, having a viscosity at 25° C. of 10 $mm^2/s$ to 1000 $mm^2/s$.

10. The mixture of claim 1, wherein at least one protonating agent is selected from the group consisting of formic acid, acetic acid, sulphuric acid, phosphoric acid, hydrochloric acid, and citric acid.

11. The mixture of claim 1, wherein the protonating agent is present in an amount of 0.2 to 1.5 mol of proton per mole of basic nitrogen atom in the $R^2$ radicals.

12. The mixture of claim 1, further comprising mono-or polyalcohols or ethers thereof.

13. A process for preparing a mixture of claim 1, wherein mixtures comprising polyorganosiloxane and silicone resins and also at most 5 parts by weight of water are diluted with water.

* * * * *

UNITED STATES PATENT AND TRADEMARK OFFICE
CERTIFICATE OF CORRECTION

PATENT NO.         : 8,907,028 B2                              Page 1 of 1
APPLICATION NO.    : 13/821333
DATED              : December 9, 2014
INVENTOR(S)        : Markus Merget et al.

It is certified that error appears in the above-identified patent and that said Letters Patent is hereby corrected as shown below:

In the Claims,

Column 10, Line 50, Claim 1:

Delete "$R^2_a R^2_b SiO_{(4-a-b)/2}$"

and insert -- $R^1_a R^2_b SiO_{(4-a-b)/2}$ --.

Signed and Sealed this
Thirty-first Day of March, 2015

Michelle K. Lee
*Director of the United States Patent and Trademark Office*